United States Patent [19]
Philippe et al.

[11] Patent Number: 5,917,088
[45] Date of Patent: Jun. 29, 1999

[54] SALICYCLIC ACID DERIVATIVES, PROCESS OF PREPARATION AND USES THEREOF

[75] Inventors: Michel Philippe, Wissous; Catherine Cohen, Paris, both of France

[73] Assignee: L'Oreal, Paris, France

[21] Appl. No.: 09/069,112

[22] Filed: Apr. 29, 1998

[30] Foreign Application Priority Data

Apr. 30, 1997 [FR] France .................................. 9705412

[51] Int. Cl.⁶ .................................................. C07C 59/90
[52] U.S. Cl. .......................................... 562/463; 514/568
[58] Field of Search ............................. 562/463; 514/568

[56] References Cited

U.S. PATENT DOCUMENTS

| | | | |
|---|---|---|---|
| 1,933,520 | 10/1933 | Bruson ........................................ | 134/57 |
| 2,431,127 | 11/1947 | Kremers .................................... | 260/521 |
| 2,481,307 | 9/1949 | Garner et al. .......................... | 260/45.75 |
| 3,657,430 | 4/1972 | Shen et al. ............................... | 424/230 |
| 3,884,949 | 5/1975 | Eicke et al. ............................ | 260/429.3 |
| 4,627,928 | 12/1986 | Karn .......................................... | 252/33 |

FOREIGN PATENT DOCUMENTS

| | | |
|---|---|---|
| 317846 | 5/1989 | European Pat. Off. . |
| 0 378 936 | 7/1990 | European Pat. Off. . |
| 0 413 528 | 2/1991 | European Pat. Off. . |
| 0 514 202 | 11/1992 | European Pat. Off. . |
| 1 210 496 | 3/1960 | France . |
| 2 053 011 | 4/1971 | France . |
| 2 207 904 | 6/1974 | France . |
| 2 581 542 | 11/1986 | France . |
| 1 093 971 | 12/1967 | United Kingdom . |
| WO 95/04519 | 2/1995 | WIPO . |
| WO 96/19182 | 6/1996 | WIPO . |
| WO 96/19184 | 6/1996 | WIPO . |
| WO 96/19228 | 6/1996 | WIPO . |
| 12597 | 4/1997 | WIPO . |

OTHER PUBLICATIONS

English Language Derwent Abstract of EP 0 378 936, Jul. 25, 1990.

English Language Derwent Abstract of FR 2 581 542.

*Primary Examiner*—Paul J. Killos
*Attorney, Agent, or Firm*—Finnegan, Henderson, Farabow, Garrett & Dunner, L.L.P.

[57] ABSTRACT

Novel salicylic acid derivatives, a process for their preparation and their use in a cosmetic or dermatological compositions.

54 Claims, 1 Drawing Sheet

FIG. 1

SALICYCLIC ACID DERIVATIVES, PROCESS OF PREPARATION AND USES THEREOF

The present invention relates to novel salicylic acid derivatives, to a process for their preparation and to their use in the cosmetic and/or dermatological fields. These derivatives can also be used in the pharmaceutical or veterinary field. More specifically, these derivatives are used as exfoliants, in particular in a composition intended to care for and/or make up human skin, mucous membranes and/or keratin fibers, in particular in order to combat the signs of ageing of the skin and/or to improve the radiance of the complexion and/or to make facial and/or body skin smooth and/or to treat wrinkles and fine lines on the skin and/or to stimulate the process of epidermal renewal and/or to treat acne and/or skin disorders.

It is known to use salicylic acid derivatives as keratolytic agents for treating acne, and as anti-ageing agents in cosmetic and/or dermatological compositions. Thus, documents FR-A-2,581,542 and EP-A-378,936 describe such derivatives.

Salicylic acid derivatives are of great value, given their biological effects on the skin, in particular on the main clinical signs of ageing of the skin, namely wrinkles and fine lines, disorganization of the "grain" of the skin, modification of the skin's complexion and loss of skin firmness and tonicity. However, the use of these derivatives poses a problem since they can cause stinging, itching and tautness after they have been applied, which may lead to considerable discomfort. Users with sensitive skin are thus often discouraged from using these compounds.

Documents WO-A-96/19184, WO-A-96/19182 and WO-A-96/19228 describe the use of water-soluble divalent strontium, manganese, magnesium lanthanide series, and calcium salts to reduce the irritation of compounds which have an irritant effect, in particular of exfoliants such as hydroxy acids. However, in these documents, the irritant active agent remains in acid form in the composition.

Moreover, document EP-A-413,528 describes the use of amphoteric compounds to reduce the irritation of hydroxy acids. According to this document, the use of inorganic salts of hydroxy acids reduces the efficacy of these hydroxy acids.

The inventors have discovered, surprisingly, novel divalent salified salicylic acid derivatives which may reduce the irritation induced by these acids. In addition, in contrast with the teaching of document EP-A-413,528, the inventors have found that these salicylic acid derivatives have properties at least equal to, if not superior to, those of the corresponding acid in free form.

A subject of the invention is thus a salified derivative of formula (I):

$$AR^- S^{2+} AR^- \tag{I}$$

in which:

$S^{2+}$ represents a divalent inorganic cation;

$AR^-$ represents the radical of formula (II):

(II)

in which:

$R_5$ represents a linear or branched, saturated or unsaturated aliphatic chain having from 3 to 15 carbon atoms, preferably from 7 to 11 carbon atoms.

Advantageously, the salicylic acid derivatives are selected from salts of 5-n-octanoylsalicylic, 5-n-decanoylsalicylic and 5-n-dodecanoylsalicylic acid. However, it is possible to use the salts of 5-propanoylsalicylic acid or of 5-n-oleylsalicylic acid.

The divalent inorganic cations are, in particular, those of the elements in columns IB, IIA, IIB, IIIB, IIIA, IVB, VB, VIB, VIIB and VIII of the Periodic Table (CAS version). The preferred divalent cations are those of columns IB, IIA, IIB, VIIB and VIII, and better still those of columns IIA, IIB and VIIB of the Periodic Table (CAS version), and in particular those of strontium, calcium, magnesium, barium and manganese.

The preferred derivatives according to the invention are the strontium salt of 5-octanoylsalicylic acid, the calcium salt of 5-octanoylsalicylic acid and the magnesium salt of 5-octanoylsalicylic acid.

A subject of the invention is also a process for manufacturing a salified derivative of formula (I), this process involving reacting a salicylic acid derivative of formula (III):

(III)

in which:

$R_5$ represents a linear or branched, saturated or unsaturated aliphatic chain having from 3 to 15 carbon atoms, with a compound containing a divalent inorganic cation, in the presence of a solvent. The compound of the invention has the particular feature, compared with the salts of the prior art, of being lipophilic.

Alcohols containing from 1 to 12 carbon atoms, and for example isopropanol and butanol, hydrocarbons such as hexane and heptane, ketones such as methyl ethyl ketone, water and, more generally, any compound capable of dissolving the acid and the compound containing the inorganic cation, such as ethers and amines, can be used as solvents.

The compound containing the inorganic cation can be selected from carbonates, bicarbonates, sulphates, glycerophosphates, borates, chlorides, nitrates, acetates, hydroxides, persulphates, salts of α-hydroxy acids (citrates, tartrates, lactates, malates) or of fruit acids, salts of amino acids (aspartate, arginate, glycocholate, fumarate), salts of fatty acids (palmitate, oleate, caseinate, behenate) and any other compound capable of releasing a divalent cation. Advantageously, a carbonate or a hydroxide is used.

A subject of the invention is also a composition comprising at least one salified derivative as defined above. This composition is, in particular, a topical composition, in particular a cosmetic and/or dermatological composition. In this case, it contains a physiologically acceptable medium. The expression physiologically acceptable medium is understood to refer to a medium which is compatible with the skin, mucous membranes (including the inside of the eyelids and the lips), the nails and/or keratin fibers (hair and eyelashes).

The derivatives according to the invention should be present in an effective amount to ensure the desired result. They can be present, for example, in a composition according to the invention in an amount preferably ranging from 0.001 to 30%, more preferably from 0.01 to 20% and better still from 0.1 to 10%, of the total weight of the composition.

The compositions containing a derivative according to the invention can be in any pharmaceutical form normally used and in particular one which is appropriate for topical application, for example in the form of an aqueous, alcoholic, aqueous-alcoholic or oily solution, an aqueous or oily gel, a liquid, pasty or solid anhydrous product, an emulsion of the water-in-oil (W/O), oil-in-water (O/W) or multiple (W/O/W or O/W/O) type, a microemulsion or a vesicle dispersion of ionic and/or nonionic type. These compositions are prepared according to the usual methods.

These compositions can be more or less fluid and can have the appearance of a white or coloured cream, an ointment, a milk, a lotion, a serum, a paste or a mousse. They can optionally be applied to the skin in the form of an aerosol. They can also be In solid form and, for example, in stick form.

These compositions can comprise at least one adjuvant selected from water, fatty substances, preserving agents, gelling agents, surfactants, emulsifiers, antioxidants, fillers, solvents, fragrances, dyestuffs, screening agents and cosmetic and/or dermatological active agents such as moisturizers, vitamins and anti-ageing active agents other than the derivatives of formula (I), and mixtures thereof. The amounts of these various additives used are those used conventionally in the cosmetic and/or dermatological field.

The fatty substances can be selected from synthetic oils, oils of animal origin, oils of plant origin, mineral oils (liquid petroleum belly), silicone oils and fluoro oils, and mixtures thereof. Fatty alcohols, fatty acids and waxes can also be used.

When the composition is an emulsion, the proportion of the fatty phase can range preferably from 5% to 80% by weight, and more preferably from 5% to 50% by weight, relative to the total weight of the composition. The oils, the waxes, the emulsifiers and the co-emulsifiers used in the composition in emulsion form are selected from those used conventionally in the cosmetic field. The emulsifier and the co-emulsifier are present in the composition in a proportion ranging from preferably 0.3% to 30% by weight, and more preferably from 0.5 to 20% by weight, relative to the total weight of the composition.

When the composition is an oily gel or solution, the fatty phase can preferably represent more than 90% of the total weight of the composition.

As emulsifiers which can be used in the invention, mention may be made, for example, of polyethylene glycol oleyl ethers such as the products sold under the names BRIJ92 and BRIJ96 by the company ICI.

The amounts of the various constituents of the compositions according to the invention are those used conventionally in the fields considered. The nature of the adjuvants and their amounts should be such that they do not modify the properties of the derivatives according to the invention.

The compositions of the invention can be used as cleansing, protective, treatment or care products and/or as make-up products for facial and/or body skin, mucous membranes and/or keratin fibers. They in particular constitute treatment or care creams for the face, for the hands or for the body (for example day creams, night creams, antisun creams), protective or care body milks, lotions (cleansing lotions, antisun lotions), skincare mousses or gels, and bath compositions. They also constitute make-up products in particular for the cheeks, the lips, the eyelashes and the eyelids, such as foundations, lip compositions and eyeshadows: to this end, they can comprise dyestuffs and in particular chemical dyes or pigments.

They can also be used for the hair in the form of aqueous, alcoholic or aqueous-alcoholic solutions or in the form of creams, gels, emulsions or mousses and in particular as haircare compositions such as shampoos, treating lotions, restructuring lotions for the hair, lotions or gels for combating hair loss, antiparasitic shampoos, etc.

The compositions according to the invention can also be solid preparations constituting cleansing bars or soaps.

As shown by the test below, the derivatives according to the invention have good exfoliant properties.

A subject of the invention is thus also the use of at least one derivative of formula (I) as an exfoliant.

Furthermore, the derivatives according to the invention have proved to be particularly suitable in caring for and/or making up human skin and/or mucous membranes and/or keratin fibers, and in particular for combating the signs of ageing of the skin and/or for improving the radiance of the complexion and/or for making facial and/or body skin smooth and/or for treating wrinkles and fine lines on the skin and/or for stimulating the process of epidermal renewal and/or for treating acne and/or for treating skin disorders.

The term skin disorders is understood to refer in particular to zona, burns, eczema, demodectic acariasis, skin ulcers, fibrosis, controlling cicatrization, psoriasis, pruritus, dermatitis, ichthyosis, corns and verrucae.

Thus, another subject of the invention is the use of at least one derivative of formula (I) in and/or for the manufacture of a cosmetic and/or dermatological composition intended to care for and/or make up the skin and/or mucous membranes and/or keratin fibers.

A subject of the invention is also the use of at least one derivative of formula (I) in and/or for the manufacture of a cosmetic and/or dermatological composition intended to combat the signs of ageing of the skin and/or to improve the radiance of the complexion and/or to make facial and/or body skin smooth and/or to treat wrinkles and fine lines on the skin and/or to stimulate the process of epidermal renewal.

A subject of the invention is also the use of at least one derivative of formula (I) in and/or for the manufacture of a cosmetic and/or dermatological composition intended for combating acne.

A subject of the invention is also the use of at least one derivative of formula (I) in the manufacture of a dermatological composition intended for combating skin disorders.

A subject of the invention is also a process for the cosmetic and/or dermatological treatment of the signs of ageing of the skin, this process involving applying at least one derivative of formula (I), in a physiologically acceptable medium, to skin showing these signs.

A subject of the invention is also a process for the cosmetic and/or dermatological treatment of acne, this process involving applying at least one derivative of formula (I), in a physiologically acceptable medium, to acneic skin.

Lastly, a subject of the invention is a process for the dermatological treatment of skin disorders, this process involving applying at least one derivative of formula (I), in a physiologically acceptable medium, to the skin.

Other characteristics and advantages of the invention will emerge more clearly from the examples, given by way of non-limiting illustration, which follow.

Examples 1 and 2 below illustrate the process for preparing derivatives in accordance with the invention.

EXAMPLE 1

Preparation of Strontium 5-Octanoylsalicylate 39.6 g of 5-octanoylsalicylic acid (0.15 mol) in 250 ml of isopropanol were introduced into a 500 ml round-bottomed flask fitted with a stirrer, a thermometer and an ascending condenser. When the dissolution was complete, 7.5 g of strontium carbonate (0.075 mol) were introduced portionwise. The medium became thick and milky; 50 ml of water were then added and the mixture was warmed to 40–45° C.

As soon as the strontium carbonate was introduced, the medium became gradually clear. The mixture was then concentrated to dryness on a rotary evaporator. 43.9 g of a white powder were obtained.

Elemental analysis: in agreement.

EXAMPLE 2

Preparation of Calcium 5-Octanoylsalicylate 39.6 g of 5-octanoylsalicylic acid (0.15 mol) in 300 ml of isopropanol and 150 ml of water were introduced into a 500 ml round-bottomed flask. 7.5 g of calcium carbonate (0.075 mol) were then added portionwise. The mixture was left stirring at room temperature for 3 hours and was then concentrated to dryness under vacuum on a rotary evaporator.

42.1 g of a white powder were obtained.

Elemental analysis: in agreement.

Formulation Example 1

Milk for the Skin, with Exfoliant Activity

| | |
|---|---|
| -Strontium 5-octanoylsalicylate | 0.5% |
| -BRIJ92 | 2.5% |
| -BRIJ96 | 2.5% |
| -Liquid petroleum jelly | 30% |
| -water | qs 100% |

The milk obtained was soft and had a good exfoliant property on the skin. TEST: The inventors observed that stimulation of the process of epidermal renewal, which includes removing the surface cells of the skin, led to a smoothing-out of marks, revival of the complexion and a reduction of wrinkles and fine lines. Thus, a compound is all the more effective in the treatment of the signs of ageing when it has a good exfoliant property. This property was demonstrated by carrying out an in vitro test of cellular detachment.

This in vitro test was carried out on keratinocytes using the composition of Example 1. The principle of the test is based on the fact that cellular detachment induces the release of corneocytes. The power of the test product to treat ageing will be proportionately greater the larger the number of corneocytes released.

The test procedure was as follows: keratinocytes were obtained from skin biopsies, by separation of the epidermis, and were dissociated by enzymatic action with trypsin and cultured at a concentration of $2\times10^5$ cells/ml. Growth and differentiation of the keratinocytes were obtained by culturing for 10 to 20 days in specific medium.

Next, after removing the culture medium, the test product was added and the activity of the product evaluated. To do this, two samples were taken at T0 and T60, i.e. before adding the product and 60 minutes after this addition, and the samples thus taken were analysed with a flow cytometer in order to count the corneocyte population. The populations of corneocytes and keratinocytes are differentiated, on a flow cytometer, by treatment with acridine orange, which is specific for cellular DNA, binds to the cell nucleus and thus exclusively reveals the presence of keratinocytes.

The cellular detachment index is determined by the difference between T60 and T0.

The same measurement was taken in comparison with the corresponding acid in free form in an analogous composition. The variation of this acid arbitrarily set the standard of 100%.

The results are collated in the table below:

| 5-Octanoylsalicylic acid $5 \times 10^{-5}$ M | Derivative of Example 1 $5 \times 10^{-5}$ M |
|---|---|
| 100% | 104.5% |

This result shows that the derivative according to the invention promotes cellular detachment at least as much as, if not more than, the free acid.

Formulation Example 2

Milk for the Skin, with Exfoliant Activity

A second composition was prepared by replacing the strontium 5-octanoylsalicylate by calcium 5-octanoylsalicylate in Formulation Example 1.

The milk obtained allowed gentle treatment of the signs of ageing of the skin.

Test: a test was carried out on isolated cornea in order to demonstrate the reduced irritation of Formulation Examples 1 and 2 when compared with an analogous composition containing free acid.

This test is based on measuring two parameters, the opacity and the permeability, changes in which reflect the attack of the tissue and thus the potential aggressiveness of the product on the isolated cornea.

The test compositions were placed in contact for 30 minutes in compartments containing isolated cornea. The opacity of the treated corneas and that of a control cornea were then measured using an opacimeter in order to determine the difference in transmission between the control cornea and the treated corneas. This difference in transmission was measured immediately after incubation and 2 hours after the first measurement; this last value T was the one taken into account.

Moreover, the corneal permeability was also measured immediately after the second opacity measurement: the compartment containing the corneas was filled with a nutrient medium to which is added a 4 mg/ml fluoresceine solution and, after a contact time of 10 minutes, the medium was removed in order to determine the optical density (OD) thereof with a spectrophotometer at 490 nm.

The corneal score was calculated from these two measurements according to the following calculation:

Corneal score=$T$+15 OD

The milder the irritation, the lower the corneal score.
The results of the test are given in Table 1 below:

TABLE 1

| TESTS at 2% | Corneal score |
|---|---|
| Example 1 | 11.9 ± 3 |
| Example 2 | 8.6 ± 3.8 |
| 5-Octanoylsalicylic acid at 0.5% | 23.5 ± 2 |
| Control | 2.4 ± 1.9 |

The significant differences between the examples according to the invention and 5-octanoylsalicylic acid show an appreciable improvement in tolerance with the derivatives according to the invention when compared with the free acid.

Moreover, another test (FIG. 1) shows that the salts of Examples 1 and 2, when applied to a reconstructed epidermis (Episkin®), show significantly lower cellular toxicity than the corresponding combinations of the free acid and a salt containing the same cation or than the free acid alone.

Figure 1:
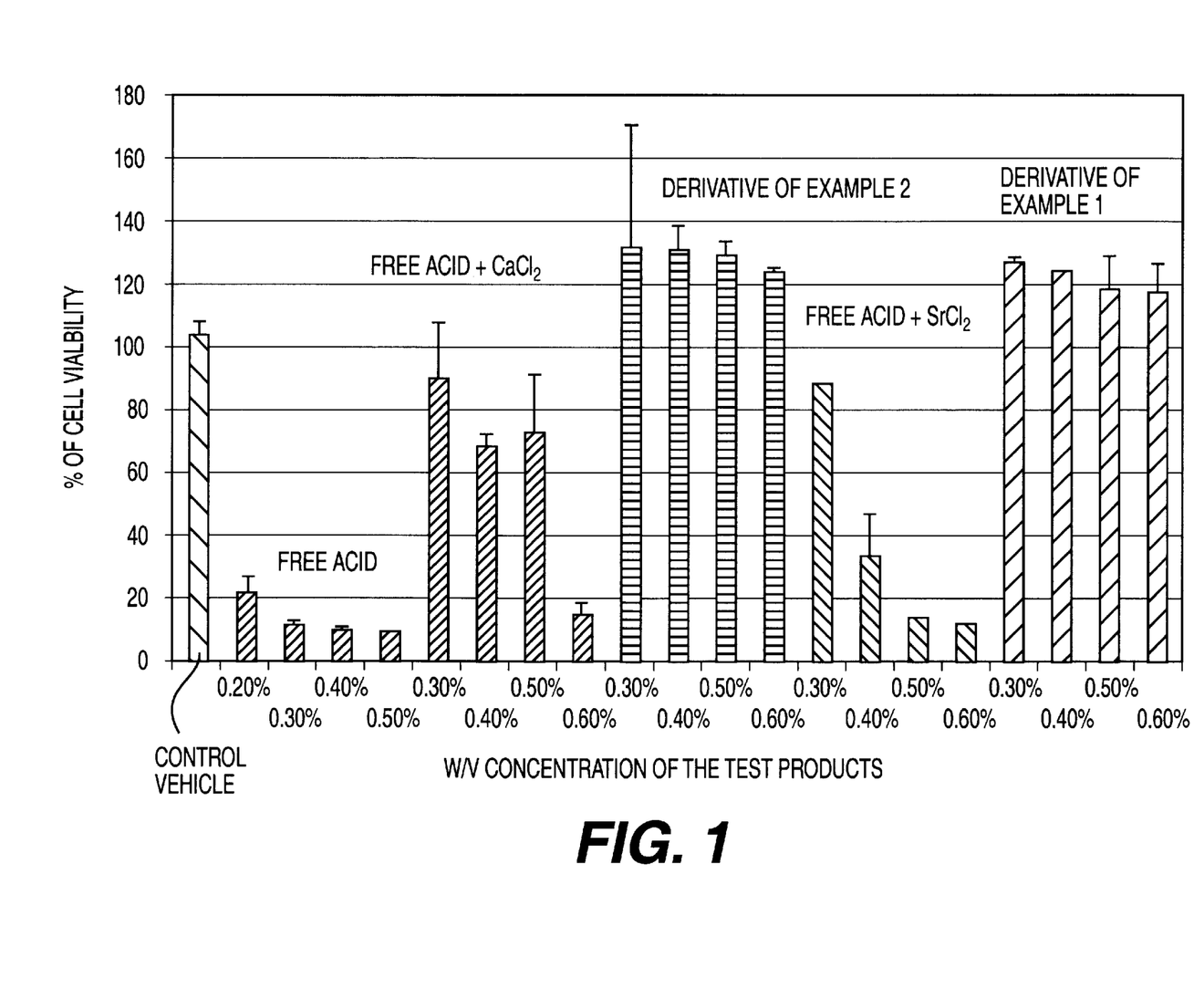

FIG. 1 shows the percentage of viability of cells as a function of the w/v concentration of the test products. From left to right, the first histogram relates to the vehicle alone, the following 4 histograms relate to the free acid, the following 4 relate to the combination of the free acid and a divalent cation salt, the divalent cation being that of the derivative according to the invention of Example 2, the following 4 histograms relate to a derivative according to the invention (Example 2), the following 4 histograms relate to the combination of the free acid and a divalent cation salt, the divalent cation being that of the derivative according to the invention of Example 1, and the final 4 histograms relate to a derivative according to the invention (Example 1).

The higher the histogram, the larger the number of living cells after 18 hours.

The results obtained were confirmed on 3 different batches of reconstructed human epidermis.

FIG. 1

Vertical axis: % of cell viability
Horizontal axis: w/v concentration of the test products under first bar: Control vehicle
From left to right in graph:
Free acid
Free acid+CaCl$_2$

Derivative of Example 2

Free acid+SrCl$_2$

Derivative of Example 1

We claim:

1. A salt of formula (I):

(I)

in which:

$S^{2+}$ represents a divalent inorganic cation;
$AR^-$ represents a radical of formula (II):

in which:

$R_5$ represents a linear or branched, saturated or unsaturated aliphatic chain having from 3 to 15 carbon atoms.

2. A salt according to claim 1, wherein $R_5$ represents a linear or branched, saturated or unsaturated aliphatic chain having from 7 to 11 carbon atoms.

3. A salt according to claim 1, wherein said salt is selected from salts of 5-n-octanoylsalicylic, 5-n-decanoylsalicylic and 5-n-dodecanoylsalicylic acid.

4. A salt according to claim 1, wherein said salt is selected from salts of 5-propanoylsalicylic acid and 5-n-oleylsalicylic acid.

5. A salt according to claim 1, wherein $S^{2+}$ represents a cation selected from cations of elements of columns IB, IIA, IIB, IIIB, IIIA, IVB, VB, VIB, VIIB and VII of the Periodic Table (CAS version).

6. A salt according to claim 5, wherein $S^{2+}$ represents a cation selected from cations of elements in columns IB, IIA, IIB, VIIB and VII of the Periodic Table (CAS version).

7. A salt according claim 6, wherein $S^{2+}$ represents a cation selected from cations of elements in columns IIA, IIB and VIIB of the Periodic Table (CAS version).

8. A salt according to claim 7, wherein $S^{2+}$ represents a cation selected from cations of strontium, calcium, magnesium, barium and manganese.

9. A salt according to claim 1, wherein said salt is selected from a strontium salt of 5-octanoylsalicylic acid, a calcium salt of 5-octanoylsalicylic acid and a magnesium salt of 5-octanoylsalicylic acid.

10. A process for preparing a salt of formula (I):

(I)

in which:

$S^{2+}$ represents a divalent inorganic cation;
$AR^-$ represents a radical of formula (II):

in which:

$R_5$ represents a linear or branched, saturated or unsaturated aliphatic chain having from 3 to 15 carbon atoms comprising the step of:

reacting, in the presence of at least one solvent, a compound of formula (III)

(III)

in which;

R$_5$ represents a linear or branched, saturated or unsaturated aliphatic chain having from 3 to 15 carbon atoms,
with at least one compound containing a divalent inorganic cation.

11. A process according to claim 10, wherein R$_5$ represents a linear or branched, saturated or unsaturated aliphatic chain having from 7 to 11 carbon atoms.

12. A process according to claim 10, wherein said at least one compound containing a divalent inorganic cation is any compound capable of releasing a divalent cation.

13. A process according to claim 10, wherein said at least one compound containing a divalent inorganic cation is selected from carbonates, bicarbonates, sulphates, glycerophosphates, borates, chlorides, nitrates, acetates, hydroxides, persulphates, salts of a-hydroxy acids and fruit acids, salts of amino acids, and salts of fatty acids.

14. A process according to claim 13, wherein said at least one compound containing a divalent inorganic cation is selected from carbonates and hydroxides.

15. A process according to claim 10, wherein said at least one solvent is selected from any compound capable of dissolving said compound of formula (III) and said at least one compound containing a divalent inorganic cation.

16. A process according to claim 10, wherein said at least one solvent is selected from alcohols containing from 1 to 12 carbon atoms, hydrocarbons, ketones, water, ethers and amines.

17. A process according to claim 16, wherein said at least one solvent is selected from isopropanol, butanol, hexane, heptane, and methyl ethyl ketone.

18. A process according to claim 17, wherein said at least one solvent is isopropanol.

19. A composition comprising an effective amount of at least one salt of formula (I):

(I)

in which:

S$^{2+}$ represents a divalent inorganic cation;

AR$^-$ represents a radical of formula (II):

(II)

in which:

R$_5$ represents a linear or branched, saturated or unsaturated aliphatic chain having from 3 to 15 carbon atoms.

20. A composition according to claim 19, wherein R$_5$ represents a linear or branched, saturated or unsaturated aliphatic chain having from 7 to 11 carbon atoms.

21. A topical composition comprising an effective amount of at least one salt of formula (I):

(I)

in which:

S$^{2+}$ represents a divalent inorganic cation;

AR$^-$ represents a radical of formula (II):

(II)

in which:

R$_5$ represents a linear or branched, saturated or unsaturated aliphatic chain having from 3 to 15 carbon atoms.

22. A cosmetic and/or dermatological composition comprising an effective amount of at least one salt of formula (I):

(I)

in which:

S$^{2+}$ represents a divalent inorganic cation;

AR$^-$ represents a radical of formula (II):

(II)

in which:

R$_5$ represents a linear or branched, saturated or unsaturated aliphatic chain having from 3 to 15 carbon atoms.

23. A composition according to claim 19, wherein said at least one salt of formula (I) is present in an amount ranging from 0.001 to 30% of the total weight of said composition.

24. A composition acccording to claim 21, wherein said at least one salt of formula (I) is present in an amount ranging from 0.001 to 30% of the total weight of said composition.

25. A composition acccording to claim 22, wherein said at least one salt of formula (I) is present in an amount ranging from 0.001 to 30% of the total weight of said composition.

26. A composition according to claim 23, wherein said at least one salt of formula (I) is present in an amount ranging from 0.01 to 20% of the total weight of said composition.

27. A composition acccording to claim 24, wherein said at least one salt of formula (I) is present in an amount ranging from 0.01 to 20% of the total weight of said composition.

28. A composition acccording to claim 25, wherein said at least one salt of formula (I) is present in an amount ranging from 0.01 to 20% of the total weight of said composition.

29. A composition acccording to claim 26, wherein said at least one salt of formula (I) is present in an amount ranging from 0.1 to 10% of the total weight of said composition.

30. A composition acccording to claim 27, wherein said at least one salt of formula (I) is present in an amount ranging from 0.1 to 10% of the total weight of said composition.

31. A composition acccording to claim 28, wherein said at least one salt of formula (I) is present in an amount ranging from 0.1 to 10% of the total weight of said composition.

32. A composition according to claim 19, wherein said composition is in the form of a fluid, a cream, an oinment, a milk, a lotion, a serum, a paste, a mousse, an aerosol, or a solid.

33. A composition acccording to claim 19, wherein said composition further comprises at least one adjuvant.

34. A composition acccording to claim 33, wherein said at least one adjuvant is selected from water, fatty substances, preserving agents, gelling agents, surfactants, emulsifiers, antioxidants, fillers, solvents, fragrances, dyestuffs, screening agents, cosmetic active agents and dermatological active agents.

35. A composition according to claim 19, wherein said composition is a cleansing product, a protective product, a treatment product, a care product, or a make-up product.

36. A method of exfoliating human skin comprising applying to said skin an effective amount of at least one composition comprising at least one salicylic acid derivative of formula (I):

(I)

in which:

$S^{2+}$ represents a divalent inorganic cation;

$AR^-$ represents a radical of formula (II):

(II)

in which:

$R_5$ represents a linear or branched, saturated or unsaturated aliphatic chain having from 3 to 15 carbon atoms.

37. A method according to claim 36, wherein $R_5$ represents a linear or branched, saturated or unsaturated aliphatic chain having from 7 to 11 carbon atoms.

38. A method of preparing a cosmetic and/or dermatological composition for caring for and/or making up skin and/or mucous membranes and/or keratin fibers comprising including in said composition at least one salicylic derivative of formula (I):

(I)

in which:

$S^{2+}$ represents a divalent inorganic cation;

$AR^-$ represents a radical of formula (II):

(II)

in which:

$R_5$ represents a linear or branched, saturated or unsaturated aliphatic chain having from 3 to 15 carbon atoms.

39. A method according to claim 38, wherein $R_5$ represents a linear or branched, saturated or unsaturated aliphatic chain having from 7 to 11 carbon atoms.

40. A method of combatting signs of ageing and/or improving the radiance of the complexion and/or smoothing facial and/or body skin and/or treating wrinkles and fine lines on the skin and/or stimulating the process of epidermal renewal comprising applying to said skin at least one composition comprising at least one salicylic acid derivative of formula (I):

(I)

in which:

$S^{2+}$ represents a divalent inorganic cation;

$AR^-$ represents a radical of formula (II):

(II)

in which:

$R_5$ represents a linear or branched, saturated or unsaturated aliphatic chain having from 3 to 15 carbon atoms.

41. A method according to claim 40, wherein $R_5$ represents a linear or branched, saturated or unsaturated aliphatic chain having from 7 to 11 carbon atoms.

42. A method of combatting acne comprising applying to acneic skin a topical composition comprising at least one salicylic acid derivative of formula (I):

(I)

in which:

$S^{2+}$ represents a divalent inorganic cation;

AR⁻ represents a radical of formula (II):

(II)

in which:

R₅ represents a linear or branched, saturated or unsaturated aliphatic chain having from 3 to 15 carbon atoms.

43. A method according to claim 42 wherein $R_5$ represents a linear or branched, saturated or unsaturated aliphatic chain having from 7 to 11 carbon atoms.

44. A method of combatting skin disorders comprising applying to skin at least one topical composition comprising at least one salicylic acid derivative of formula (I):

$$AR^-S^{2+}AR^- \quad (I)$$

in which:

$S^{2+}$ represents a divalent inorganic cation;
AR⁻ represents a radical of formula (II):

(II)

in which:

R₅ represents a linear or branched, saturated or unsaturated aliphatic chain having from 3 to 15 carbon atoms.

45. A method according to claim 44, wherein $R_5$ represents a linear or branched, saturated or unsaturated aliphatic chain having from 7 to 11 carbon atoms.

46. A process for cosmetically treating signs of ageing of the skin comprising applying to said skin, in a physiologically acceptable medium, at least one salicylic acid derivative of formula (I):

$$AR^-S^{2+}AR^- \quad (I)$$

in which:

$S^{2+}$ represents a divalent inorganic cation;

AR⁻ represents a radical of formula (II):

(II)

in which:

R₅ represents a linear or branched, saturated or unsaturated aliphatic chain having from 3 to 15 carbon atoms.

47. A process according to claim 46, wherein $R_5$ represents a linear or branched, saturated or unsaturated aliphatic chain having from 7 to 11 carbon atoms.

48. A process for cosmetically treating acne comprising applying to acneic skin, in a physiologically acceptable medium, at least one salicylic acid derivative of formula (I):

$$AR^-S^{2+}AR^- \quad (I)$$

in which:

$S^{2+}$ represents a divalent inorganic cation;
AR⁻ represents a radical of formula (II):

(II)

in which:

R₅ represents a linear or branched, saturated or unsaturated aliphatic chain having from 3 to 15 carbon atoms.

49. A process according to claim 48, wherein $R_5$ represents a linear or branched, saturated or unsaturated aliphatic chain having from 7 to 11 carbon atoms.

50. A process for dermatologically treating skin disorders comprising applying to said skin in a physiologically acceptable medium at least one salicylic acid derivative of formula (I):

$$AR^-S^{2+}AR^- \quad (I)$$

in which:

$S^{2+}$ represents a divalent inorganic cation;

AR⁻ represents a radical of formula (II):

(II)

in which:

R₅ represents a linear or branched, saturated or unsaturated aliphatic chain having from 3 to 15 carbon atoms.

51. A process according to claim 50, wherein $R_5$ represents a linear or branched, saturated or unsaturated aliphatic chain having from 7 to 11 carbon atoms.

52. A skin wrinkle treatment composition comprising in a physiologically acceptable medium at least one salicylic acid derivative of formula (I):

(I)

in which:

$S^{2+}$ represents a divalent inorganic cation;
AR– represents a radical of formula (II):

(II)

in which:

R₅ represents a linear or branched, saturated or unsaturated aliphatic chain having from 3 to 15 carbon atoms.

53. An acne skin treatment composition comprising in a physiologically acceptable medium at least one salicylic acid derivative of formula (I):

(I)

in which:

$S^{2+}$ represents a divalent inorganic cation;
AR– represents a radical of formula (II):

(II)

in which:

R₅ represents a linear or branched, saturated or unsaturated aliphatic chain having from 3 to 15 carbon atoms.

54. A skin exfoliant treatment composition comprising in a physiologically acceptable medium at least one salicylic acid derivative of formula (I):

(I)

in which:

$S^{2+}$ represents a divalent inorganic cation;
AR– represents a radical of formula (II):

(II)

in which:

R₅ represents a linear or branched, saturated or unsaturated aliphatic chain having from 3 to 15 carbon atoms.

* * * * *

UNITED STATES PATENT AND TRADEMARK OFFICE
CERTIFICATE OF CORRECTION

PATENT NO. : 5,917,088
DATED : June 29, 1999
INVENTOR(S) : PHILIPPE et al.

It is certified that error appears in the above-identified patent and that said Letters Patent is hereby corrected as shown below:

In claim 13, column 9, line 27, "a-hydroxy" should read --α-hydroxy--.

Signed and Sealed this

Twenty-first Day of December, 1999

Attest:

Q. TODD DICKINSON

Attesting Officer        Acting Commissioner of Patents and Trademarks